United States Patent [19]

Kaye

[11] 4,027,973

[45] June 7, 1977

[54] DETECTOR APPARATUS FOR LASER LIGHT SCATTERING PHOTOMETERS

[75] Inventor: Wilbur I. Kaye, Fullerton, Calif.

[73] Assignee: Beckman Instruments, Inc., Fullerton, Calif.

[22] Filed: July 2, 1973

[21] Appl. No.: 375,930

[52] U.S. Cl. .................................. 356/73; 250/239; 250/574; 356/103; 356/201

[51] Int. Cl.² ........................................ G01N 21/22

[58] Field of Search ............ 250/239, 574; 356/73, 356/103, 104, 201, 218, 225

[56] References Cited

OTHER PUBLICATIONS

Wilbur Kaye et al., *Applied Optics* vol. 12, No. 3, Mar. 1973, pp. 541–550.

*Primary Examiner*—John K. Corbin
*Assistant Examiner*—F. L. Evans
*Attorney, Agent, or Firm*—R. J. Steinmeyer; R. R. Meads; J. R. Shewmaker

[57] ABSTRACT

Detector apparatus for a laser light scattering photometer of the type for measuring radiant power scattered from a sample at a selectable angle with respect to the direction of an incident beam of radiant power and for measuring radiant power transmitted through the sample in the direction of the incident beam. The improved detector apparatus receives and detects the scattered power and the transmitted power and provides an output indicative of the radiant power of each independent of the spatial properties of the two beams. The detector apparatus comprises a planar diffuser spaced from and parallel to the large area end-window of a photomultiplier detector, the diffuser diffusing the energy over the surface of the end-window. The diffuser and photomultiplier detector are positioned within a cylindrical container which is enclosed at the end thereof in front of the diffuser, the enclosed end of the container having an aperture therein through which the beams pass to the diffuser. By making the inside surface of the cylindrical container, and the end thereof, highly reflective, the energy which is reflected from the end-window of the detector is reflected back thereto preventing a loss of sensitivity. A high pass filter-spacer may be positioned between the diffuser and the photomultiplier to reduce the detector's sensitivity to ambient light, such sensitivity being further reduced by the container, into which the ambient light can pass only through the aperture therein.

6 Claims, 2 Drawing Figures

DETECTOR APPARATUS FOR LASER LIGHT SCATTERING PHOTOMETERS

BACKGROUND OF THE INVENTION

1. Field of the Invention

The present invention relates to detector apparatus for laser light scattering photometers and, more particularly, to apparatus for receiving and detecting scattered and transmitted power issuing from a sample in a laser light scattering photometer and for providing an output indicative of the received radiant power irrespective of a spatial difference between the two beams.

2. Description of the Prior Art

Inhomogeneity in the polarizability of liquids and solids leads to the scattering of an incident beam of light. Since this inhomogeneity extends to molecular dimensions, it can be used to characterize the size, motion, and thermodynamic behavior of molecules. The inhomogeneity may be consequence of fluctuations in concentration or density or may simply result from interfaces between molecular aggregates of different polarizability or refractive index. Consequently, light scattering can be used to study solutions, dispersions, and surfaces.

The intensity of scattered radiant energy depends upon the wavelength of the incident radiant energy, the polarizability of the particles or molecules compared with that of the medium in which they are suspended, and on the size and concentration of the particles. It has also been found that the intensity of the radiant energy scattered in the forward direction by a single particle will be proportional to the square of its volume and independent of its shape if the particle is isotropic and if its dimensions are small compared to the wavelength of the incident radiant energy. Since the forward radiant energy scattered by a dispersion containing particles is greater as the individual particles become larger, the size of the particles may be determined from the intensity of the radiant energy scattered when the refractive indices of the particles and of the medium are known. In a similar manner, the scattering properties associated with particle size have been adapted to the determination of the molecular weights of large molecules.

Light scattering is potentially faster, more accurate, and applicable over a wider molecular-weight range than other techniques employing viscosity, osmometry, or gravitational sedimentation. However, several problems have plagued light scattering measurements. In the first instance, the solutions have to be clarified—freed of particles—a procedure that has sometimes required days of preparation. Secondly, large volumes of sample have been required.

The light scattering technique most frequently employed for molecular weight determination involves preparation of a Zimm plot. Extrapolation of the Zimm plot to zero angle and zero concentration permits the determination of the weight average molecular weight. Unfortunately, this extrapolation to zero angle is subject to large errors when the angular function is non-linear and when particles contaminate the sample. Molecular weights above a few million are particularly difficult to determine because of uncertainties in the extrapolation to zero angle.

These measurements would be facilitated and accuracy would be improved if they could be obtained directly at very low angles and concentrations. These problems have stimulated numerous efforts to develop instruments operating at small scattering angles and small sample volumes. Unfortunately, the minimum scattering angle of most commercial light scattering photometers is 20°–30°. Attempts to reduce the scattering angle in custom instruments have been limited to 10°–15° because background signals from unwanted reflections and particulate contaminants increase rapidly with a decrease in scattering angle.

One of the most recent developments in this rapidly evolving field is the measurement of light scattered at small forward angles using a laser as the source of illuminating radiant energy. The laser provides a narrow beam of intense radiant energy which is both monochromatic and coherent in nature. The narrow beam permits scattering measurement at small angles relative to the incident direction of the laser beam. The intensity of the radiant energy contained in the beam enables greater sensitivities than photometer instruments not employing the laser as a source.

Perhaps the greatest advantage of the use of a laser for molecular weight determination is in minimizing the clarification problem. Defraction of incident light scattered by foreign particles of a size comparable to the wavelength of light increases drastically as the scattering angle $\theta$ decreases. This problem is a major contributor to the hazard in extrapolating the Zimm plot to zero angle. However, a laser beam can be focused to a small diameter, achieving an extremely small scattering volume. Typical scattering volumes encountered heretofore were approximately 1 ml whereas this has been reduced to $10^{-4}$ to $10^{-6}$ ml in a laser photometer. As a result, the probability of a foreign particle residing within the scattering volume is proportionately reduced. Because of the high power density, any particle within the scattering volume scatters intensely and its presence is obvious.

The small sample volume required to fill the sample cell further facilitates sample clarification. Sample volumes about 1,000 times less than that of cells in conventional variable angle instruments have been possible. Obviously, with less sample to filter, the clarification can be accomplished in a shorter period of time, an important factor when performing kinetic measurements. The short-path cells also minimize problems of sample absorption. Furthermore, the cell design permits use of flowing filtered samples without allowing them to contact the air.

Another area benefited by the laser is micro-fluorescence spectroscopy. The monochromatic lines of the laser are useful for exciting fluorescence in a variety of materials and the fact that the beam from these lasers can be focused to a very small spot provides the potential for measurements concerning fluorescence of microscopically small samples. Another application related to fluorescence is the study of excitation and deexcitation processes of the triplet states in organic molecules.

A low angle laser light scattering photometer is described in an article entitled "Light Scattering Measurements on Liquids at Small Angles" by W. I. Kaye, A. J. Havlik, and J. B. McDaniel, Polymer Letters, Volume 9, pages 695–699 (1971). Improvements in this photometer are described in an article entitled "Low Angle Laser Light Scattering—Absolute Calibration" by W. I. Kaye and A. J. Havlik, Applied Optics, Volume 12, No. 3, pages 541–550 (March, 1973) and in an article entitled "Low-Angle Laser Light Scattering" by W. I. Kaye, Analytical Chemistry, Volume 45, No. 2, pages 221A–225A (February, 1973). These articles describe a low angle laser light scattering photometer including a helium-neon laser operating in the $TEM_{00}$ mode, the rays from which are focused by a lens onto a sample confined between two thick silica windows and a black Teflon spacer. Certain of the rays scattered from the sample through an angle θ, defined by an annulus, are focused by a relay lens onto a field stop. Rays passing through the field stop are focused by an objective lens onto the end-window of a photomultiplier detector. The output of the detector is proportional to the total radiant power falling thereon, $P_\theta$.

The primary laser beam, attenuated by suitable attenuators, is transmitted through the sample, in the direction of the incident beam, and is focused by the relay lens onto the field stop. These rays, having a radiant power $P_0$, are then focused by the objective lens onto the end-window of the photomultiplier detector. The ratio $P_\theta/P_0$ is utilized to determine the Rayleigh factor, $R_\theta$, which is then utilized to calculate the molecular weight.

Since $P_\theta \simeq 10^{-9}P_0$, it is necessary that the photomultiplier detector have high sensitivity. Furthermore, since the curve of molecular weight versus concentration, which must be extrapolated to zero concentration, is a linear function only at very low concentrations, very low concentrations must be used, requiring high instrument sensitivity if the number of measurements are to be minimized. Rapid kinetic measurements also require high sensitivity.

The detector must exhibit spatial uniformity since the scattered beam and the transmitted beam are incident on the detector at different angles and are of different cross-sectional areas. However, problems have been encountered in the past in that existing photomultipliers generate different signal levels when two beams are incident directly thereon at different angles. Furthermore, the sensitivity (amperes per watt) of most photocathodes varies significantly with the position of the cathode illuminated.

One approach to the solution of this problem has been to enlarge the size of the beam since this has an integrating effect. However, this has been an undesirable solution in laser photometers where it is desirable to minimize the sample size and the scattering volume.

It has also been suggested to use an integrating sphere or a diffuser plate to spread the incident scattered and transmitted energy over the surface of the photomultiplier. Integrating spheres have been unacceptable in low angle instruments because of the resultant loss of sensitivity. Furthermore, instruments that use diffusers assume that the areas of the detected transmitted and scattered beams cancel each other. However, this situation prevails only if the illuminating beam is well collimated, the beam is of uniform intensity, the detector does not see past the edges of the illuminated sample, and the detector sensitivity is constant over the illuminated area of the photocathode. To insure these conditions, the optical system becomes very inefficient in the sense that few of the potentially available photons emitted by the source can be detected. Thus, this approach too has been unacceptable in low angle instruments.

SUMMARY OF THE INVENTION

In accordance with the present invention, there is provided detector apparatus for low angle laser light scattering photometers which solves these problems in a manner unattainable heretofore. The present detector apparatus is completely compatible with a small beam, a small sample size, and a small scattering volume. The present detector apparatus operates to distribute the detected scattered and transmitted beams over the entire area of an end-window photomultiplier detector so as to achieve a high degree of spatial uniformity. Furthermore, such spatial uniformity is achieved with no loss in detector sensitivity. The present detector apparatus also results in a reduced sensitivity to ambient light.

Briefly, the present invention represents an improvement to a laser photometer of the type for measuring radiant power scattered from a sample at a selectable angle with respect to the direction of an incident beam of radiant power and for measuring radiant power transmitted through the sample in the direction of the incident beam, the photometer including a converging lens for focusing the scattered and the transmitted beams into converging conical beams thereby concentrating the intensity of the beams into coplanar and approximately coincident points at the apices of said beams. The improved detector apparatus receives and detects the scattered power and the transmitted power and provides an output indicative of the radiant power of each independent of the spatial properties of the two beams.

A planar diffuser positioned in the plane of the apices of the beams diffuses the coverging conical beams. The large area end-window of a photomultiplier detector is spaced from and parallel to the diffuser with a high pass filter-spacer therebetween to properly space the diffuser from the end-window of the detector and to reduce sensitivity to ambient light. The diffuser, spacer, and photomultiplier detector are positioned within a cylindrical container being enclosed at the end thereof in front of the diffuser, the enclosed end of the container having an aperture therein through which the beams pass to the diffuser, the aperture also reducing sensitivity to ambient light. By making the inside surface of the cylindrical container, and the end thereof, highly reflective, the energy which is reflected from the end-window and the inside of the detector is reflected by the container back to the detector so that the detector assembly is as sensitive as its spatially averaged response when the beam falls directly on the photocathode, but without a significant level of spatially variable sensitivity.

OBJECTS

It is therefore an object of the present invention to provide detector apparatus for laser light scattering photometers.

It is a further object of the present invention to provide apparatus for receiving and detecting scattered and transmitted power issuing from a sample in a laser light scattering photometer and for providing an output indicative of the received radiant power irrespective of a spatial difference between the two beams.

It is a still further object of the present invention to provide detector apparatus for laser light scattering photometers which provides spatial uniformity with no loss in sensitivity.

It is another object of the present invention to provide detector apparatus for laser light scattering photometers which has reduced sensitivity to ambient light.

It is still another object of the present invention to provide detector apparatus for laser light scattering photometers which is suited for use with small beams, small sample sizes, and small scattering volumes.

Still other objects, features, and attendant advantages of the present invention will become apparent to those skilled in the art from a reading of the following detailed description of the preferred embodiment constructed in accordance therewith taken in conjunction with the accompanying drawings wherein like numerals designate like parts in the several figures and wherein:

DESCRIPTION OF THE PREFERRED EMBODIMENTS

Figure 1:
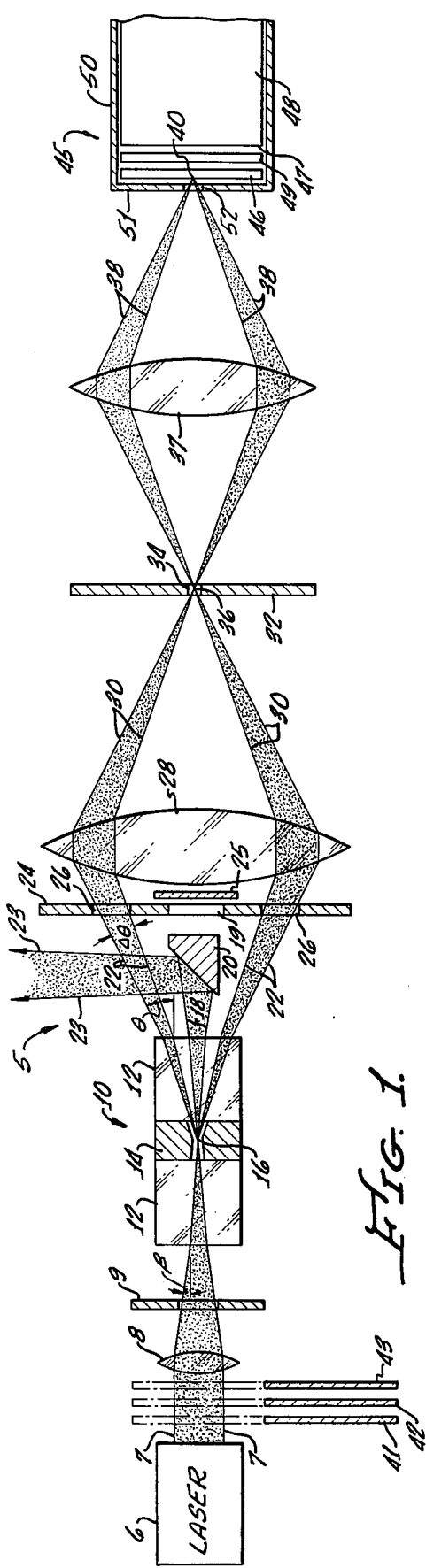
FIG. 1 is a cross-sectional view of the optical elements of a low angle laser light scattering photometer as used for measuring radiant power scattered from a sample at small forward angles relative to the direction of the incident beam, with the present improved detector apparatus in use.

Referring now to the drawings, a low angle laser light scattering photometer of the type described previously, generally designated 5, includes a source of radiant energy 6 which generates a beam of radiant energy defined by the rays 7. Radiant energy source 6 is preferably a helium-neon laser operating in the $TEM_{00}$ mode. The beam from laser 6 is converged by a converging device 8, such as a refractive or reflective lens or an element of similar nature and characteristics, to a small spot or point 16 within a sample container 10 thereby irradiating a sample contained therein with an intense beam of radiant energy. The angle of convergence $\beta$ of the beam is generally small since the smallest angle $\theta$ relative to the direction of the incident beam at which scattered radiant energy from a sample may be measured without intercepting a portion of the transmitted incident beam is equal to $2\beta$. Source mask and aperture 9, which is located closely adjacent converging device 8, intercepts a predetermined amount of the converging beam along with other undesired radiant energy to more accurately define the converging beam passing therethrough.

Sample container 10 includes two thick silica windows 12 with a black Teflon spacer 14 therebetween. A small hole in the spacer serves as an aperture and forms a cell wall, point 16 being centered within such aperture. The cell volume with a 2.5 mm fixed spacer 14 is less than 0.010 ml so that both the sample size and the scattering volume is small. Samples are typically introduced through hypodermic needles inserted in spacer 14. The windows 12 are highly polished to reduce scattering.

With reference to FIG. 1, radiant energy issuing from the sample within spacer 14 and exiting from sample container 10 at a given angle $\theta$ is illustrated by rays 22. Rays 18 which are transmitted through sample container 10 and are a continuation of the undeflected incident rays are partially reflected as rays 23 from a radiant energy trap 20, with the remaining energy being absorbed by trap 20. Trap 20 may be a dark or black glass cylinder which adsorbs radiant energy that enters and which has a 45° surface to partially reflect energy incident thereon at an angle of 90° with respect to the direction of incidence. The combined features of the absorbing glass and 45° surface produce a radiant energy trap substantially more effective than the Rayleigh horn or cone traps and black glass attenuators used heretofore.

Figure 2:
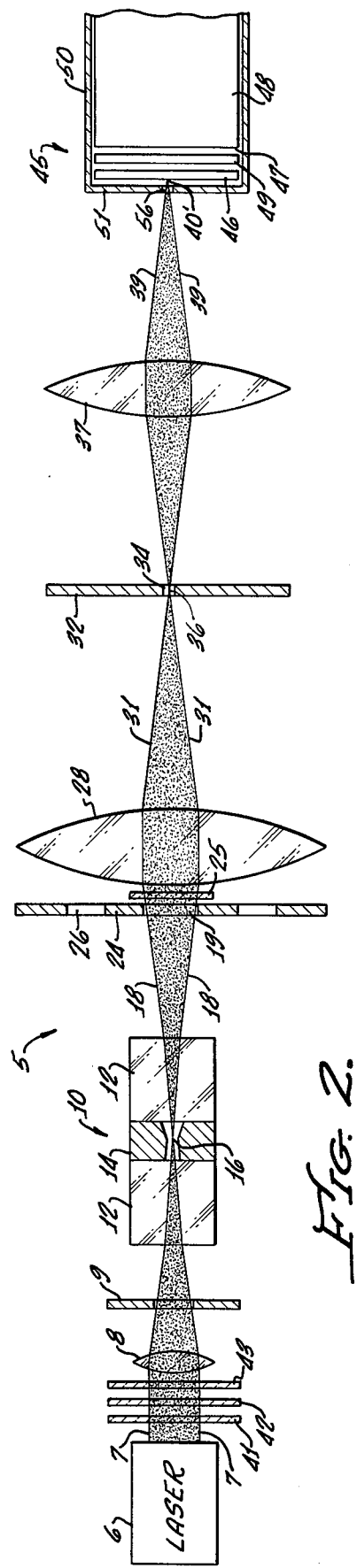
FIG. 2 is a cross-sectional view of the optical elements of the photometer of FIG. 1 as used for measuring radiant power transmitted through a sample in the direction of the incident beam, with the present detector apparatus in use.

As shown in FIG. 2, when it is desired to obtain a measurement of the transmitted incident radiant power defined by rays 18, trap 20 is removed and the rays are permitted to pass through a central aperture 19 in a mask 24.

Returning now to FIG. 1, rays 22 issuing from the sample within spacer 14 in an incremental angle $\Delta\theta$ at a given angle $\theta$ are intercepted by an annular aperture 26 in radiant energy mask 24. Annular aperture 26 is symmetrically located about the axis of the incident beam so that the annular aperture 26 receives all of the energy issuing from the sample at angle $\theta$ in a conical surface having an apex at point 16 and a base formed by aperture 26.

The radiant energy designated by rays 22 intercepted by annular aperture 26 in mask 24 are directed to a converging device 28 where the radiant energy designated by rays 30 are converged into a conical surface having an apex at a point 36. The size of point 36 will depend upon the size of point 16 since point 36 is an image of point 16. Although the converging means 28 illustrated is a refractive lens, other converging apparatus may be employed such as circular reflective mirror, fiber optics, or other devices of similar nature and characteristics.

Referring again to FIG. 2, the radiant energy defined by rays 18 which pass through aperture 19 in mask 24 when trap 20 is removed pass through an attenuator 25 to converging device 28 where the radiant energy designated by rays 31 are converged into a conical surface having an apex at point 36. Attenuator 25 is a safety attenuator to prevent damage to equipment and injury to personnel when trap 20 is removed. Additional calibrated attenuators 41, 42, and 43 may be positioned between source 6 and converging device 8 for insertion in the path of the beam from source 6 when trap 20 is removed. Attenuators 41–43 would be calibrated to reduce the intensity of the beam, when measuring the transmitted energy, to the approximate value of the intensity of the beam when measuring the scattered energy. For example, attenuators 41–43 might attenuate the beam by a factor of $10^{-9}$.

A field stop 32 having an aperture 34 therein is positioned such that aperture 34 coincides with point 36 thereby allowing the radiant energy focused onto point 36 to pass through field stop 32. Therefore, and as shown in FIG. 1, light trap 20, radiant energy mask 24, converging device 28, and field stop 32 combine to admit through aperture 34 only the energy issuing from the sample at the given angle $\theta$ and to essentially eliminate other undesired radiant energy. By making the windows 12 of sample cell 10 of such thickness that the outer surfaces thereof are displaced from point 16 by a predetermined distance, radiant energy scattered therefrom will be intercepted by the opaque portion of field stop 32 and will be prevented from passing beyond field stop 32. The advantage of displacing the surfaces of windows 12 in such a manner is that surface scratches and surface contaminants produced through use will not interfere with scattering measurements. It should be recognized, however, that refraction in the thick cell windows, which is not effectively illustrated in the drawings due to the small angles involved, changes the effective angle $\theta$ of scatter from the sample and changes the point of focus 16. This effect must be taken into account in the positioning of the various components.

With reference to FIGS. 1 and 2, the radiant energy passing through aperture 34 in field stop 32 is directed to a converging device 37 where the radiant energy designated by rays 38 and 39 in FIGS. 1 and 2, respectively, is converged into conical surfaces having an apex at points 40 and 40' which are approximately coincident. Points 40 and 40' are made to coincide with detector apparatus, generally designated 45, where the scattered energy and the transmitted energy are received and detected to provide an output indicative of the radiant power in each beam.

Heretofore, many types of detectors have been used having a sensitivity compatible with the wavelength of interest and a receiving area compatible with the optical design. Detectors used heretofore are photodiodes, photomultipliers, phototubes, or other devices of similar nature and characteristics.

In use, and with reference to FIG. 1, rays 7 from laser source 6 are focused by converging device 8 onto a sample confined within sample container 10. Certain of the rays scattered from the sample through an angle $\theta$, defined by annulus 26 in mask 24, are focused by converging device 28 onto aperture 34 of field stop 32. Rays passing through field stop 32 are focused by converging device 37 onto the end-window of a photomultiplier detector. The output of the detector is proportional to the total radiant power falling on the photocathode, $P_\theta$. At this time, the transmitted energy is blocked by trap 20.

Thereafter, trap 20 is removed and the rays 7 from laser source 6, attenuated by attenuators 41–43, are transmitted through the sample in the direction of the incident beam and after passing through aperture 19 in mask 24 and attenuator 25 are focused by converging device 28 onto field stop 32. The rays passing through field stop 32 are focused by converging device 37 onto the photocathode of the photomultiplier detector. The output of detector is proportional to the total radiant power falling on the photocathode, $P_0$. The ratio $P_\theta/P_0$ is utilized to determine the Rayleigh factor, $R_\theta$, which is then utilized to calculate the molecular weight.

Since $P_\theta \simeq 10^{-9} P_0$, it is necessary that detector apparatus 45 have high sensitivity. Furthermore, since the curve of molecular weight versus concentration, which must be extrapolated to zero concentration, is a linear function only at very low concentrations, very low concentrations must be used, requiring high instrument sensitivity of the number of measurements are to be minimized.

Still further, it will be observed from a comparison of FIGS. 1 and 2 that the scattered beam and the transmitted beam are incident on detector apparatus 45 at different angles. Furthermore, points 40 and 40' for the scattered and transmitted beams may not exactly coincide. Since the outputs of available photomultipliers will vary as the angle of incidence and the point of incidence varies, the resultant ratio $P_\theta/P_0$ cannot be utilized to accurately determine the Rayleigh factor unless these factors are compensated for. While various types of compensation have been attempted in the past, all have resulted in a loss of sensitivity, which is unacceptable in low angle measurements.

According to the present invention, detector apparatus 45 is constructed so as to provide spatial uniformity with no loss in sensitivity. Detector apparatus 45 comprises a planar diffuser 46 positioned in the planes of points 40 and 40'. Diffuser 46 is located a short distance in front of the large area end-window 47 of a photomultiplier detector 48. A spacer 49 between diffuser 46 and end-window 47 establishes the required spacing. Diffuser 46 may be an opal diffuser which diffuses the light from rays 38 and 39 over the surface of end-window 47 of detector 48.

Since diffuser 46 scatters the light in the scattered and transmitted beams, much of the light striking end-window 47 will be reflected. To prevent the loss of sensitivity due to this reflected light, diffuser 46, spacer 49, and photomultiplier detector 48 are positioned coaxially within a cylindrical container 50 having an enclosed end 51 adjacent diffuser 46. Enclosed end 51 has an aperture 52 therein through which rays 38 and 39 pass to diffuser 46. Detector aperture 52 is larger than aperture 34 in field stop 32 and does not vignette any desired rays. End 51 of container 50 serves to reduce the sensitivity of detector 48 to light leaks, the only ambient light which can pass to the large end-window 47 of detector 48 being that which passes through aperture 52.

In accordance with the present invention, the inside surfaces of container 50 and enclosed end 51 are made highly reflective. In this manner, the energy reflected from end-window 47 is trapped within the chamber defined by end-window 47, the inner surface of container 50, and the inner surface of enclosed end 51, such rays being reflected by container 50 and enclosed end 51 back to end-window 47. Thus, by making the detector side of enclosed end 51 highly reflecting, the sensitivity of detector apparatus 45 is maintained.

Means (not shown) are also provided for maintaining the potential of container 50 at the potential of the cathode of photomultiplier detector 48. Thus, container 50 also functions as an electrostatic shield for detector 48.

Spacer 49 may be a high pass or band pass filter, thereby functioning not only to properly space diffuser 46 from end window 47 but also to reduce the sensitivity of detector 48 to ambient light.

Thus, the combination of a large area end-window photomultiplier 48 with a diffuser 46 and spacer 49 inside of a highly reflective cavity defined by container 50 and enclosed end 51 results in equal sensitivity of detector 48 to the transmitted and scattered beams. Aperture 52 being small, the sensitivity of detector 48 to ambient light is reduced. By making spacer 49 a high pass filter, the sensitivity of detector 48 to ambient light is reduced still further. Finally, container 50 may also function as an electrostatic shield for detector 48.

While the invention has been described with respect to the preferred physical embodiments constructed in accordance therewith, it will be apparent to those skilled in the art that various modification and improvements may be made without departing from the scope and spirit of the invention. Accordingly, it is to be understood that the invention is not to be limited by the specific illustrative embodiments, but only by the scope of the appended claims.

I claim:

1. In a laser photometer for measuring radiant power scattered from a sample at a selectable angle with respect to the direction of an incident beam of radiant power and for measuring radiant power transmitted through the sample in the direction of said incident beam, said photometer including means for focusing said scattered and said transmitted power into converging conical beams, the improvement comprising means for receiving and detecting said scattered power and said transmitted power and for providing a spatially uniform output indicative of the radiant power of each, said means comprising:

a planar diffuser positioned in the plane of the apices of said conical beams to diffuse said converging beams;

a detector having a large area end-window spaced from and parallel to said diffuser; and a cylindrical container surrounding said diffuser and said detector, said cylindrical container being enclosed at the end thereof adjacent said diffuser, said enclosed end of said container having an aperture therein through which said beams pass to said diffuser, the inside surfaces of said cylindrical container and said enclosed end being highly reflective whereby the energy reflected from said end-window is reflected by said inside surfaces back to said end-window of said detector.

2. In a laser according to claim 1, the improvement wherein said diffuser is an opal diffuser which diffuses the radiant energy over the surface of said end-window of said detector.

3. In a laser photometer according to claim 1, the improvement further comprising:

a spacer disc positioned between said diffuser and said end-window of said detector for properly spacing said detector from said diffuser.

4. In a laser photometer according to claim 3, the improvement wherein said spacer comprises:

a high pass or band pass filter for reducing the response of said detector to ambient light.

5. In a laser photometer according to claim 1 including a field stop between said sample container and said focusing means, the improvement wherein said aperture in said enclosed end of said cylindrical container is larger than the aperture in said field stop.

6. In a laser photometer according to claim 1 wherein said detector is a photomultiplier detector, the improvement further comprising:

means for maintaining said cylindrical container at the electrical potential of the cathode of said photomultiplier detector.

* * * * *